United States Patent [19]

Kiovsky et al.

[11] 4,006,177
[45] Feb. 1, 1977

[54] METHANATION CATALYST RECOVERY

[75] Inventors: Thomas E. Kiovsky; Milton M. Wald, both of Houston, Tex.

[73] Assignee: Shell Oil Company, Houston, Tex.

[22] Filed: Oct. 3, 1975

[21] Appl. No.: 619,543

[52] U.S. Cl. .................. 260/449 M; 260/449.6 M
[51] Int. Cl.² .......................................... C07C 27/06
[58] Field of Search ................... 260/449 M, 449.6

[56] References Cited

UNITED STATES PATENTS 2,714,116  7/1955  Teichmann et al. ............ 260/449.6

*Primary Examiner*—James O. Thomas, Jr.
*Assistant Examiner*—A. Siegel
*Attorney, Agent, or Firm*—Dean F. Vance

[57] ABSTRACT

A sulfur resistant methanation catalyst and the process to recover the same are disclosed. The catalyst comprises a molten metal salt carrier selected from the class consisting of the halides of zinc and cadmium, and mixtures thereof, melting below 1000° C, said molten salt having dispersed therein one or more catalytically active metals selected from the group consisting of iron, molybdenum, manganese, nickel, cobalt, zinc, titanium, silver, copper and thorium. The recovery process comprises separating the metal sulfide, contacting the sulfide with a hydrogen halide at a reduced temperature, and recycling the resultant molten metal salt halide to the methanation reactor.

14 Claims, No Drawings

METHANATION CATALYST RECOVERY

BACKGROUND OF THE INVENTION

Catalytic methanation is a well-known reaction which is widely employed in the chemical and energy providing industries. Probably its most widespread current and potential application is in the treatment of the gaseous effluent from the gasification or partial oxidation of carbonaceous fuels with oxygen and/or water, e.g., steam-hydrocarbon reforming and partial combustion of liquid and solid carbonaceous fuels, to produce a hydrogen-rich gas for chemical synthesis, e.g., ammonia manufacture, or petroleum refining, e.g., catalytic hydrocracking and hydrogenation, or to form a methane-rich gas having high BTU value and low CO content for use in residential and industrial heating or power generation. In the former case, the gasification or partial oxidation effluent, which typically contains substantial quantities of $H_2$, CO, $CO_2$ and $H_2O$ as well as $N_2$ in cases where air is used as the oxidant source, is generally subject to a process known as the carbon-monoxide shift-conversion reaction prior to catalytic methanation. In this case the CO-shift reaction converts a substantial quantity of the CO present to $H_2$ and $CO_2$ by reaction with $H_2O$ in the presence of a catalyst and the primary purpose of catalytic methanation is to remove small quantities of CO which remain in the hydrogen-rich product gas by conversion to methane in order to avoid poisoning of downstream processing catalysts. In the latter case, i.e., conversion of partial oxidation effluent gas to methane-rich gas, the gasification or partial oxidation effluent gas is subject to CO-shift to obtain the appropriate ratio of $H_2$ to CO (usually 3 to 1) and the CO-shift product gas in then subject to catalytic methanation for conversion of carbon oxides and hydrogen contained therein to methane. In either case, the CO-shift effluent gas is subject to an intermediate processing step to remove sulfurous materials in cases where a sulfur-containing carbonaceous fuel feedstock is employed since all commercially used methanation catalysts are highly sensitive to poisoning by sulfur compounds.

Because of the increasing demand for a high BTU, clean gas as an energy source in the United States and the acknowledged decreasing and finite nature of natural gas reserves in the United States as well as happenings on the world scene which make energy self-sufficiency desirable or even essential, there has been a dramatic increase in interest in the manufacture of a clean, high BTU gas energy source which will meet pipeline standards by synthetic means for alternative carbonaceous resources such as coal or heavy hydrocarbons. Many of the more attractive synthetic approaches which have been proposed are based on gasification or partial combustion of the carbonaceous material, and, as indicated above, include catalytic methanation as part of the integrated process scheme to upgrade the BTU value of the product gas to a level acceptable for pipeline gas applications. CO and $H_2$ have heating values of about 300 BTU/ft³ whereas pipeline natural gas has a value near 1000 BTU/ft³. While a number of metallic species are known to be active and selective methanation catalysts including, inter alia, nickel, ruthenium, cobalt, iron and molybdenum, their application to the manufacture of high BTU or pipeline gas has been less than satisfactory for several reasons which relate to the physical form of the catalyst employed and/or the nature of the methanation reaction, itself.

In the first place, the primary thrust of previous efforts to effect catalytic methanation has been to utilize the active catalyst in solid form as a finely-divided particulate on a refractory support, i.e., nickel on alumina or kieselguhr being pre-eminent, or as an alloy in a fixed or fluidized bed. These catalyst types are highly susceptible to deactivation via carbon deposition which can only be partially remedied by operation at undesirably high $H_2$/CO mole ratios in the feed gas. Furthermore, methanation reactions with these catalyst systems generally must be limited to temperatures below 400° C to avoid sintering and deactivation of the catalyst and the highly exothermic nature of the methanation reaction itself provides severe operational difficulties in controlling catalyst temperature in a fixed or fluidized bed at these levels when the CO concentration of the feed gas is in the range required for methane-rich gas manufacture. As an aside, the use of the fixed or fluidized bed catalyst processing techniques also make it difficult to recover any substantial quantity of the heat generated in the methanation for use in other phases of the process, e.g., the endothermic gasification in steam gasification of coal. Finally, the methanation reaction itself, is considered to be a combination of several reactions including the primary reaction (1)

$$3 H_2 + CO \longrightarrow CH_4 + H_2O \quad (1)$$

and secondary reactions (2) and (3)

$$2 H_2 + 2CO \longrightarrow CH_4 + CO_2 \quad (2)$$

$$4 H_2 + CO_2 \longrightarrow CH_4 + 2H_2O \quad (3)$$

whose thermodynamic equilibria are such that the equilibrium yield of methane is adversely effected at high temperatures, i.e., above 500° C; reaction (2) being a combination of reaction (1) and the water gas shift reaction (4).

$$CO + H_2O \longrightarrow CO_2 + H_2 \quad (4)$$

Thus, with conventional catalyst systems, methanations have been limited to the lowest temperatures consistent with acceptable catalyst activity in part, because of catalyst instability at high temperatures, the highly exothermic nature of the methanation reaction and the inability to effect an equilibrium shift towards methane, e.g., by absorption of one of the reaction products, at high temperatures under practical circumstances. A good review of previous efforts in catalytic methanation and the problems associated therewith can be found in G. A. Mill et al., "Catalytic Methanation", *Catalysis Reviews*, 8(2), 159–210 (1973).

Accordingly, it would be desirable if an active catalyst system for methanation at temperatures above 500° C could be developed which would minimize operational problems associated with high temperature operation of the solid, particulate catalysts of the prior art, e.g., carbon deposition, instability and heat removal, while at the same time somehow shifting the methanation equilibrium towards methane formation, e.g., by $H_2O$ absorption from the reaction mass, at these high temperatures. This would be especially advantageous when catalytic methanation is utilized in conjunction with, for example, steam gasification of coal for the production of methane-rich gas. This is because the coal gasification reaction is high temperature but endothermic, thus requiring substantial input of high temperature heat such as that which could be recovered from an exothermic methanation reaction carried out at high temperatures. Furthermore, the reaction effluent from such coal gasification is many times already at or close to the thermodynamic equilibrium concentration of methanation reactants in a high temperature methanation reaction scheme, due to the high steam concentration of the gaseous effluent, and as such cannot be catalytically promoted towards methane formation unless one of the reaction products, particularly $H_2O$, is absorbed out of the reaction mass during or prior to methanation. It would also be very beneficial if the catalyst system employed were sulfur resistant. In that case, it would be possible to eliminate, or reduce the severity of, the intermediate desulfurization step typically employed before the methanation reaction.

The Prior Art

One improved methanation catalyst system is disclosed in our copending patent application entitled High Temperature Methanation with Molten Salt-Based Catalyst System, Ser. No. 546,371, filed Feb. 3, 1975. The catalyst system disclosed in application Ser. No. 546,371 is a molten metal salt-based catalyst system comprising a molten metal salt carrier selected from the class consisting of the halides and carbonates of alkali metals and alkaline earth metals and the halides of zinc, copper, manganese, cadmium, tin and iron, and mixtures thereof, melting below 1000° C, said molten salt having dispersed therein one or more catalytically active metals selected from the class consisting of iron, molybdenum, manganese, nickel, cobalt, zinc, titanium, silver, copper and thorium in the form of finely-divided elemental metals, metal oxides and/or metal carbides.

While the catalyst system disclosed in copending application Ser. No. 546,371, is an effective methanation catalyst, it is necessary to desulfurize the gaseous feed prior to contacting the feed with the methanation catalyst so as to prevent the premature deactivation of the catalyst. For example, the catalytic activity of iron and potassium chloride salts containing an iron carbonyl compound declines rapidly as soon as a sulfur-containing feed is introduced. Likewise a catalyst comprising the eutectic melt of lithium, sodium and potassium chlorides with a cobalt carbonyl activator showed greatly reduced activity after the addition of only a few millimoles of $H_2S$ in the reactant gas mixture.

It has now been found that catalysts containing molten zinc and cadmium halide salts are sufficiently sulfur resistant to be employed in a methanation reaction where the gaseous reactant mixture contains sulfur compounds.

SUMMARY OF THE INVENTION

The present invention is a continuous process for the production of methane from a sulfur containing gaseous reactant mixture containing hydrogen, carbon monoxide and/or carbon dioxide which comprises:

1. contacting said gas mixture in a reaction zone maintained at temperatures above about 500° C with a molten metal salt-based catalyst system comprising a molten metal salt carrier selected from the class consisting of the halides of zinc and cadmium, and mixtures thereof, melting below 1000° C, said molten salt having dispersed therein one or more catalytically active metals selected from the group consisting of iron, molybdenum, manganese, nickel, cobalt, zinc, titanium, silver, copper and thorium in the form of finely-divided elemental metals, metal oxides and/or metal carbides, wherein a gaseous product mixture is formed and a portion of the molten metal salt halide is converted to a metal sulfide (a sulfide of the metal salt) to form a metal salt mixture, 2. separating the gaseous product mixture from the metal salt mixture, 3. separating the metal sulfide from a portion of the metal salt mixture and recycling the remainder of the metal salt mixture to the reaction zone, 4. reacting the metal sulfide thus separated with a hydrogen halide at a temperature of between about 50° C and about 400° C in an amount stoichiometrically equivalent to the separated metal sulfide thereby converting a stoichiometric portion of the metal sulfide to a metal salt halide and recovering the same, and 5. recycling the metal salt halide formed in step 4 to the reaction zone.

The catalyst systems disclosed are less susceptible to carbon deposition than previous catalyst systems, exhibit little, if any, catalyst sintering and inactivation at high temperatures and provide a superior means for reducing the problems associated with heat transfer from the exothermic methanation reaction since the molten salt carrier functions as both a heat sink and a heat exchange medium for the reaction. Furthermore, the molten salt carriers of the invention are effective in absorbing water from the methanation reaction mass at high temperatures, and, as such, function to shift the reaction equilibrium towards methane which is especially critical in cases such as steam gasification of coal where the reactant mass approaches equilibrium concentration of reactants and reaction products at the high temperature methanation conditions, without an intermediate $H_2O$ removal step. Most importantly, the catalysts disclosed are rugged, sulfur-tolerant methanation catalysts that can be easily regenerated according to the process of the present invention.

DESCRIPTION OF THE PREFERRED EMBODIMENTS

The Catalyst

The high temperature methanation catalysts according to the invention are heterogeneous catalyst systems comprising a molten metal salt carrier which melts below 1000° C, but is stable under methanation reaction conditions at temperatures above 500° C, preferably about 500° to about 800° C, and which contains a uniform dispersion of a finely-divided metal, metal oxide and/or metal carbide of certain metallic species which exhibit catalytic activity for hydrogenation of carbon oxides or methanation. To function as an effective carrier of the heterogeneous catalyst system, it is essential that the metal salt melt be thermally and chemically stable under methanation reaction zone conditions. That is, the molten salt or salt mixture must not be hydrolyzed significantly with steam at temperatures above 500° C nor be reduced by the methanation reactant feed mixture under the conditions prevailing in the reaction zone. Preferably, the metal salt or salt mixture melts below about 700° C and most preferably between about 100° and 600° C. Suitable metal salts or salt mixtures include the halides of zinc and cadmium or mixtures thereof. Most preferred because of their availability and/or favorable effect on the activity of the active metallic species in the catalyst system are the zinc halides, e.g., zinc chloride, zinc bromide and zinc iodide. The zinc halides are emminently suitable as molten catalyst carriers in the methanation of gaseous reactant mixtures containing substantial quantities of water such as that derived from the steam gasification of coal since they absorb up to 90% or more of the water present in a typical gasification effluent at methanation temperatures above 500° C and thereby shift the methanation equilibrium towards methane formation.

The active catalytic species in the molten salt-based methanation catalysts according to the invention are finely-divided metals, metal oxides and/or metal carbides of certain transition and actinide elements and zinc which are uniformly dispersed in the molten carrier. While this group of catalytically active metals does include certain metallic species which have heretofore been described as having catalytic activity in methanation reactions, e.g., nickel and iron, it is not completely apparent that the instant dispersed solid catalysts function in a manner equivalent to the prior art supported catalysts. This is because only certain of the known methanation catalysts are active in the molten salt-based catalysts of the invention and a metal, zinc, not previously considered to have catalytic methanation activity is, in fact, quite active as a methanation catalyst in the molten-salt based systems of the instant invention. The metals which show catalytic methanation activity when dispersed as finely-divided elemental metals, metal oxides and/or metal carbides in the molten salt-based catalysts of the invention include iron, molybdenum, manganese, nickel, cobalt, zinc, titanium, silver, copper and thorium. Of these catalytically active metals, iron, zinc, manganese, nickel, cobalt and molybdenum seem to provide the highest activity and are preferred for that reason. Most preferred for reasons of availability and activity are zinc and iron. As indicated above, the solid metallic catalyst is present in the molten salt carrier as the elemental metal, metal oxide and/or metal carbide. Usually it is present as a mixture of all three chemical forms with the elemental metal and metal oxide being predominant. While the exact particle size of the finely-divided catalyst in the molten salt carrier is not considered critical to the operability of the invention, it appears that this average particle size diameter should not exceed about 0.5 mm, if optimum results are to be obtained.

The concentration of active metal catalyst dispersed in the molten salt-based catalyst systems of the invention is not critical and will depend, in part, on the concentration of carbon oxides and hydrogen in the reactant gas; the purpose and extent of methanation desired, i.e., production of methane-rich, high BTU gas or conversion of CO to methane in the production of a hydrogen-rich synthesis gas; and process conditions such as reactant feed rates, temperatures, pressures, etc. For most applications, the concentration of active metal catalyst dispersed in the molten salt carrier will range from about 0.1% to about 20% by weight of the total (catalyst + carrier) catalyst composition. Preferably, in cases where the catalyst is employed to upgrade partial oxidation or gasification effluent gas to methane-rich, high BTU gas, the catalyst concentration will range from about 5% to about 15% by weight of the total catalyst composition. As indicated previously, this catalyst concentration may be composed of a single catalytically active metal or a mixture of one or more of such metals. Preferred metal mixtures include zinc-iron, iron-manganese and zinc-manganese.

The active catalysts according to the invention may be prepared by simple physical comminution of the metal catalysts, in the form of relatively pure elemental metals or metal oxides, to the desired particle size, e.g., hammer mill grinding, and subsequent addition of the ground metal or metal oxide powder to the metal salt carrier before or after heating to, or above, its melting point. Alternatively, the active metal catalysts may be prepared by adding the catalytically active metal to the metal salt before or after heating in the form of a compound or complex which will thermally and/or chemically decompose at methanation temperatures into the desired metal and/or metal oxide. Examples of suitable metal compounds or complexes which will decompose to yield the desired metal or metal oxide at methanation temperatures, e.g., 500° C or above, include inorganic metal hydroxides and salts such as nitrates and carbonates; organic salts or carboxylic acids such as formate, trifluoroacetate, butrate, 2-ethylhexanoate, lactate and citrate; organometallic compounds and complexes as metallocenes, e.g., ferrocene, metal carbonyls, e.g., iron pentacarbonyl, molybdenum hexacarbonyl, etc., and metal complexes such as those derived from pyridine and the metal acetate or 1-5-cyclooctadiene and the metal nitrate. It is also possible to prepare the dispersed metal or metal oxide in situ in the molten salt medium by adding two chemical compounds which will react, e.g., zinc bromide and sodium carbonate, in the molten medium to yield the desired active catalyst, e.g., zinc oxide. In this alternative method of preparing the active catalyst, the thermally and/or chemically decomposable metal compound or complex is preferably added to the metal salt carrier after the carrier has been heated to or above its melting point (usually about 400° C or above) and the molten salt or salt mixture is agitated for a time period ranging from 10 to 120 minutes to allow the metal compound or complex time to decompose and disperse in the molten medium. Preferred metal compounds or complexes for use in this procedure include the metal carbonyls and metallocenes. In this case, the gaseous reactants can be contacted by the molten catalyst system prior to decomposition of all of the metal catalyst compound or complex precursor, since the precursor will continuously decompose and release active catalyst during the course of the methanation reaction.

The Methanation Reaction

The gaseous reactant feed to the catalytic methanation process of the invention must contain at least some measurable amount of hydrogen and carbon oxides (carbon dioxide and/or carbon monoxide). Preferably, the reactant feed mixture to methanation contains both hydrogen and carbon monoxide at an $H_2$:CO mole ratio of 2:1 with $H_2$:CO reactant mole ratios of 3:1 or more being most preferred. Gaseous reactant feed mixtures which can be suitably methanated with catalyst compositions of the instant invention typically contain 10 to 99.9% $H_2$, 0.1 to 50% CO, 0 to 20% $CO_2$, 0 to 70% $H_2O$, 0 to 25% $CH_4$ and 0 to 70% $N_2$. Such gaseous reactant feed mixtures are quite suitably obtained from conventional partial oxidation or gasification of carbonaceous fuels such as, inter alia, natural gas or normally gaseous hydrocarbons, e.g., $C_{2-4}$ saturated and olefinic hydrocarbons; heavier hydrocarbon fractions including gasoline, kerosene, naphtha, distillates, gas oils and residual oils; solid or semi-solid fuels including coal, oil shale, partial combustion soot and bituminous residues from petroleum refining. Typically, the partial oxidation or gasification effluent gas will be subject to a conventional CO-shift reaction to adjust the hydrogen to carbon monoxide mole ratio and an optional particulate removal step, e.g., one or more cyclone separators, prior to methanation according to the invention. However, at least the intermediate CO-shift step is not essential to the preparation of a suitable gaseous feedstock for use in the invention since conversion of reactants to methane will still be effected to the extent that the stoichiometry of the reaction can be satisfied.

One of the preferred applications of the catalytic methanation process of the instant invention is in the upgrading of methane-rich gas derived from the partial oxidation or gasification of coal. Several coal gasification processes employing non-catalytic gasifiers in which coal is converted to a crude product gas containing principally $CH_4$, $H_2$, CO, $H_2O$ and $CO_2$ by high temperature reaction with steam and oxygen are quite well known, e.g., the Lurgi process, the Koppers-Totzek process, etc., and need not be detailed herein. A catalytic steam gasification process for conversion of coal to methane-rich gas by reaction with steam in the presence of certain alkali carbonate catalysts at about 600°–750° C is described in U.S. Pat. No. 3,686,240 to Aldridge et al. In general, all of these coal gasification processes are endothermic in the gasification stage and produce a suitable gas feed mixture for methanation according to the instant invention even though the $H_2O$ content may range as high as 50% by weight of the feed mixture, a value at or near methanation equilibrium for conventional supported methanation catalysts. This feed mixture is suitable for high temperature methanation with the instant catalysts because, as indicated previously, the molten salt carriers of the instant invention have the ability to absorb up to over 90% of the water present in the methanation feed gas, thereby shifting the reaction equilibrium towards methane. It is especially preferred that the instant methanation process be utilized to upgrade the methane content of the gaseous effluent derived from a coal-steam gasification process such as that described in the aforementioned U.S. Pat. No. 3,686,240 since the endothermic gasification takes place at a temperature approximating the exothermic methanation temperature. Thus, it is possible to utilize the heat generated by methanation via for example, heat exchange between the molten salt carrier and the gasification reaction zone, to at least partially satisfy the heat requirements of the gasification reaction.

Procedurally, the methanation process of the instant invention can be suitably effected by any conventional technique for intimately contacting a gaseous reactant feed with a molten or fluid catalyst. Such techniques include batch or continuous procedures wherein the gas is introduced into the vapor phase of a reaction chamber or autoclave containing the molten salt-based catalyst and the catalyst is agitated into contact with the gas mixture. In the case of a batch reaction according to this procedure, the product gas is merely withdrawn at the end of the reaction (measured by time and/or pressure drop) whereas in the case of a continuous reaction the size of the reaction chamber and catalyst to gas mass ratios in the reaction chamber are selected to allow sufficient gas-molten medium contact prior to continuous withdrawal of product gas at some point in the vapor phase remote from the reactant feed port. Alternatively, the gas phase can be bubbled through a mass of molten catalyst in a reaction chamber or autoclave or passed into countercurrent contact with the catalyst phase in a vertically-oriented contacting column. In any case, the methanation reaction zone is maintained at temperatures above about 500° C while the gaseous reactant feed mixture is in contact with the catalyst. Preferably, the methanation reaction according to this invention is effected at temperatures between about 500° and 900° C and most preferably between about 600° and 800° C. The pressures employed in the methanation reaction according to the invention generally range between 100 psig and 1500 psig and preferably between 400 and 1200 psig.

The reaction or gas-molten salt contact time is not considered critical to the operation of the methanation process of the instant invention, provided sufficient time is alloted to facilitate absorption of water into the molten salt carrier and mass transfer and absorption of the gaseous reactants on to the active catalytic species dispersed in the molten carrier. Accordingly, the reaction time should be at least 10 seconds with reaction times of about 10 minutes being a reasonable maximum for practical operation. Preferably, the reaction time ranges from about 0.5 to about 5 minutes. In this regard, the ratio of volume of reactant feed gas to molten salt-based catalyst is continuous processes employing the methanation catalysts of the invention may suitably range from about 100 to about 5000 per hour (gas measured at STP).

The Catalyst Regeneration

With the typical methanation catalyst it is essential that either a desulfurized carbonaceous fuel be employed for manufacture of the reactant gas or that the reactant gas be subject to a conventional desulfurization procedure, i.e., scrubbing with liquid or solid absorbents for sulfur compounds (mainly $H_2S$) prior to contact with the methanation catalyst. However, by employing the catalysts of the present invention, it is possible to reduce the severity of the desulfurization procedure, or even eliminate the necessity for a desulfurization procedure, thereby increasing the sulfur content of the gaseous reactant feed, while still maintaining a high catalytic activity.

The present catalyst systems are sulfur tolerant because the $H_2S$ present in the gaseous reactant feed at methanation temperatures above 500° C preferentially reacts with the zinc or cadmium halide to form a zinc or cadmium sulfide solid and a hydrogen halide gas. Since the $H_2S$ preferentially reacts with the molten metal salt carrier, the activity of the catalytically active metal dispersed in the carrier is not drastically effected. For example, relative stabilities of zinc and iron sulfides and bromides are consistent with this explanation (see equation below):

$$FeS + ZnBr_2 \rightleftharpoons ZnS + FeBr_2 \quad \Delta F = -7 \text{ Kcal/mole}$$

The catalysts employed in the present invention are also tolerant to high levels of ammonia. Significantly, even though zinc chloride retains ammonia more strongly than other zinc halides and is more strongly poisoned by ammonia (at least in coal hydrocracking) the activity of the molten zinc chloride based catalysts according to the present invention are relatively unaffected by the presence of ammonia in amounts ranging up to about 1 mole of ammonia per three moles of salt.

Eventually, after a significant portion of the molten metal salt carrier is converted to sulfide form, the activity of the catalyst lessens and it becomes necessary to regenerate the catalyst. Various processes to regenerate zinc halide catalysts have been proposed, e.g., U.S. Pat. Nos. 3,371,049, 3,625,861, and 3,790,469. However, these processes require a number of complex operations not necessary in the present invention.

The regeneration procedure according to the present invention comprises cooling the metal salt mixture (containing zinc or cadmium sulfide as well as halide) to a temperature of between about 50° and about 400° C, preferably about 50° to about 150° C, reacting the cooled metal salt mixture with a hydrogen halide thereby converting a portion of the metal sulfide to a molten metal salt halide, and recycling the resulting mixture to the reaction zone. In a preferred embodiment only a portion of the metal salt mixture is cooled and regenerated, thereby reducing the heating and cooling requirements of the regeneration process.

The regeneration temperature is critical because at the temperature of the methanation reaction, equilibrium favors formation of metal sulfide and hydrogen halide while at the lower temperature of regeneration, equilibrium favors formation of metal halide and hydrogen sulfide. This relationship is evident from the values for free energy shown in the equation below:

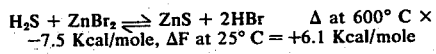
$$H_2S + ZnBr_2 \rightleftharpoons ZnS + 2HBr \quad \Delta \text{ at } 600°C \times -7.5 \text{ Kcal/mole}, \Delta F \text{ at } 25°C = +6.1 \text{ Kcal/mole}$$

The H₂S gas released in the regeneration is typically separated and routed to a sulfur recovery unit.

The hydrogen halide employed in the regeneration is obtained from any convenient source. In some situations, it is desirable to add the hydrogen halide as an aqueous solution. If desired, the hydrogen halide released in the methanation reaction may be recovered from the gaseous product stream, e.g., by fractionation, and then be used in the regeneration step. In this manner, the net loss of hydrogen halide is greatly reduced.

As stated above, one of the important attributes of the catalysts according to the present invention is their ability to absorb large quantities of water thereby shifting the equilibrium towards the formation of methane. Accordingly, at some point in the overall methanation process, it becomes necessary to remove the water absorbed by the molten metal salt carrier. In a preferred embodiment, an inert gas, e.g., nitrogen, is employed to strip away volatiles such as water and ammonia from the regenerated catalyst. Under certain conditions it is also possible to employ air as the stripping gas.

The types of reaction vessels and separation vessels employed in the present invention are generally known to those skilled in the art (see, e.g., U.S. Pat. No. 3,790,469) and need not be detailed here.

The invention is further illustrated by means of the following Illustrative Embodiments and Comparative Examples. Note that the embodiments and examples are given for purposes of illustration only and that the invention is not to be regarded as limited to any of the specific conditions or reactants recited therein.

In all embodiments and examples, the feed gas employed contained carbon monoxide and hydrogen in a molar ratio of approximately 2:1. Activity is expressed in terms of either conversion or initial rate. Conversion is defined as the percentage of moles of carbon monoxide converted to methane. Initial rate is expressed as the decline in pressure (psig) per minute. The catalysts were prepared by adding the catalytically active metal to the metal salt before heating in the form of a compound which thermally or chemically decomposes at methanation temperatures into the desired metal and/or metal oxide.

Illustrative Embodiment I

A zinc bromide salt containing iron pentacarbonyl as the active metal catalyst was employed in a methanation reaction at 600° C and 400 psig with a feed gas containing 1% volume H₂S. The amount of catalyst employed was approximately 1300 millimoles of ZnBr₂ and 150 milligram atoms of iron. No decline in catalyst activity was witnessed after 5 hours of operation, equivalent to approximately 60 millimoles of H₂S in the feed gas. The product gas showed only traces of H₂S. Addition of further H₂S caused a slow loss of catalyst activity so that after addition of 95 millimoles of H₂S, conversion had dropped to about 28% from the original value of 45%.

Further, it was found that the activity of the partially sulfur-poisoned ZnBr₂-iron catalyst was restored by the addition of more iron pentacarbonyl, indicating that while H₂S fed as a gas is a catalyst poison, zinc sulfide formed from it is not. Support for this conclusion was obtained when 5% weight zinc sulfide was added to zinc iodide based catalyst with no effect on activity.

Illustrative Embodiment II

Illustrative Embodiment II was conducted in a similar manner to Illustrative Embodiment I, except that ferrocene was employed instead of iron pentacarbonyl. Conversion declined slowly from 40% to 32% after 9.5 hours with 1% H₂S in the feed gas (119 millimoles H₂S).

Illustrative Embodiment III

In Illustrative Embodiment III, a zinc chloride melt containing iron derived from Fe(CO)₅ as the active metal catalyst was employed in a methanation reaction at 600° C and 400 psig with a feed gas containing 1% H₂S. Ammonia was also present with the catalyst. Initial conversion was between about 26–30%. No decline in conversion was noted over a run of over 4 hours.

Illustrative Embodiment IV

A zinc iodide melt containing manganese as the active metal was employed at 600° C and 400 psig with a feed gas containing 10% H₂S. The initial conversion was 40%. During the run a slow decline in conversion was noted until after about 40 minutes (28 millimoles H₂S) the conversion has dropped to about 35%.

Comparative Example I

Comparative Example I reveals the results of adding small amounts of sulfide to catalyst systems not containing zinc or cadmium halides as the molten salt. In all cases the methanation pressure was about 400 psig. The results are presented below in Table I. In runs 3 and 4, the molten salt was the eutectic melt of lithium, sodium and potassium carbonates. In runs 5 and 6, the reaction temperature was 550° C while in runs 1–4, 7 and 8, the reaction temperature was 600° C.

Table I

| Run No. | Molten Salt | Catalyst Type | Millimoles | Sulfide Type | Millimoles | Initial Rate (psig/minute) 500° C | 600° C |
|---|---|---|---|---|---|---|---|
| 1 | FeCl₂/NaCl | Fe(CO)₅ | 100 | None | | 23 | |
| 2 | FeCl₂/NaCl | Fe(CO)₅ | 100 | Na₂S | 2 | 4 | |
| 3 | M₂CO₃ | Mo(CO)₆ | 50 | None | | 12 | 49 |
| 4 | M₂CO₃ | Mo(CO)₆ | 50 | H₂S | 1 | — | 1.3 |
| 5 | LiCl/LiF | Fe(CO)₅ | 100 | None | | 79 | |
| 6 | LiCl/LiF | Fe(CO)₅ | 100 | H₂S | 1 | 1.6 | |
| 7 | FeCl₂/NaCl | Fe(OH)₂ | 50 | None | | 22 | |
| 8 | FeCl₂/NaCl | Fe(OH)₂ | 50 | H₂S | 1.3 | 0.8 | |

We claim as our invention:

1. A continuous process for the production of methane from a sulfur containing gaseous mixture containing hydrogen, carbon monoxide and/or carbon dioxide which comprises:
   a. contacting said gaseous mixture in a reaction zone maintained at temperatures above about 500° C with a molten metal salt-based catalyst system comprising a molten metal salt carrier selected from the group consisting of the halides of zinc and cadmium, and mixtures thereof, melting below 1000° C, said molten salt having dispersed therein one or more catalytically active metals selected from the group consisting of iron, molybdenum, manganese, nickel, cobalt, zinc, titanium, silver, copper and thorium in the form of finely-divided elemental metals, metal oxides and/or metal carbides, wherein a gaseous product mixture is formed and a portion of the molten metal salt halide is converted to a metal sulfide to form a metal salt mixture.
   b. separating the gaseous product mixture from the metal salt mixture,
   c. separating a portion of the metal salt mixture and recycling the remainder of the metal salt mixture to the reaction zone,
   d. reacting the portion of the metal salt mixture thus separated with a hydrogen halide at a temperature of between about 50° C and about 400° C in an amount stoichiometrically equivalent to the metal sulfide contained in the separated metal salt mixture thereby converting a stoichiometric portion of the metal sulfide to a metal halide, and
   e. recycling the regenerated portion of the metal salt mixture containing the metal halide formed in step (d) to the reaction zone.

2. The process according to claim 1 wherein the molten metal salt carrier is a zinc halide.

3. The process according to claim 2 wherein the molten metal salt carrier is zinc chloride.

4. The process according to claim 2 wherein the zinc halide is zinc bromide.

5. The process according to claim 2 wherein the gaseous reactant mixture contains hydrogen and carbon monoxide at an H₂:CO mole ratio of at least 2:1, the reaction zone is maintained between about 500° and about 900° C; and the concentration of catalytically active metal dispersed in the molten metal salt carrier is from about 0.1 to about 20.0% by weight of the total catalyst composition.

6. The process according to claim 5 wherein said metal sulfide is reacted with said hydrogen halide at a temperature of between about 50° C and about 150° C.

7. The process according to claim 5 wherein the catalytically active metal is zinc or iron.

8. The process according to claim 5 wherein a portion of the metal salt mixture is stripped with an inert gas at a temperature of about 300° C to about 500° C to remove any volatile materials present.

9. The process according to claim 5 wherein the metal halide formed in step (d) is stripped with an inert gas at a temperature of about 300° C to about 500° C to remove any volatile materials present.

10. A continuous process for the production of methane from a sulfur containing gaseous reactant mixture containing hydrogen, carbon monoxide and/or carbon dioxide which comprises:
    a. contacting said gas mixture in a reaction zone maintained at temperatures above about 500° C with a molten metal salt-based catalyst system comprising a molten metal salt carrier selected from the group consisting of the halides of zinc and cadmium, and mixtures thereof, melting below 1000° C, said molten salt having dispersed therein one or more catalytically active metals selected from the group consisting of iron, molybdenum, manganese, nickel, cobalt, zinc, titanium, silver, copper and thorium in the form of finely-divided elemental metals, metal oxides and/or metal carbides, wherein a gaseous product mixture is formed and a portion of the molten metal salt halide is converted to a metal sulfide to form a metal salt mixture,
    b. separating the gaseous product mixture from the metal salt mixture,
    c. cooling the metal salt mixture to a temperature between about 50° C and about 400° C,
    d. reacting the cooled metal salt mixture with a hydrogen halide thereby converting at least a portion of the metal sulfide to a metal salt halide, and
    e. recycling the metal salt mixture from step (d) to the reaction zone.

11. The process according to claim 10 wherein the molten metal salt carrier is a zinc halide.

12. The process according to claim 11 wherein the zinc halide is zinc bromide, the catalytically active metal is zinc or iron, the gaseous reactant mixture contains hydrogen and carbon monoxide at an H₂:CO mole ratio of at least 2:1, the reaction zone temperature is between about 500° C and about 900° C, and the concentration of catalytically active metal dispersed in the molten salt carrier is from about 0.1 to about 20.0% by weight of the total catalyst composition.

13. The process according to claim 12 wherein a portion of the metal salt mixture is stripped with an inert gas at a temperature of about 300° C to about 500° C to remove any volatile materials present.

14. The process according to claim 12 wherein the metal salt halide formed in step 9 (d) is stripped with an inert gas at a temperature of about 300° C to about 500° C to remove any volatile materials present.

* * * * *